(12) United States Patent
Owa

(10) Patent No.: US 7,746,468 B2
(45) Date of Patent: Jun. 29, 2010

(54) ANALYSIS SYSTEM

(75) Inventor: Michiaki Owa, Kyoto (JP)

(73) Assignee: Shimadzu Corporation, Kyoto-fu (JP)

( * ) Notice: Subject to any disclaimer, the term of this patent is extended or adjusted under 35 U.S.C. 154(b) by 41 days.

(21) Appl. No.: 12/331,755

(22) Filed: Dec. 10, 2008

(65) Prior Publication Data

US 2009/0153865 A1 Jun. 18, 2009

(30) Foreign Application Priority Data

Dec. 13, 2007 (JP) ............................ 2007-322358

(51) Int. Cl.
*G01J 3/42* (2006.01)
(52) U.S. Cl. ...................................... 356/326
(58) Field of Classification Search ................. None
See application file for complete search history.

(56) References Cited

U.S. PATENT DOCUMENTS 6,714,241 B2 * 3/2004 Baer .......................... 348/241
7,140,766 B2 * 11/2006 Glukhovsky et al. ........ 374/175

FOREIGN PATENT DOCUMENTS

| JP | 08-122150 A | 5/1996 |
| JP | 11-118781 A | 4/1999 |
| JP | 2005-257575 A | 9/2005 |

* cited by examiner

Primary Examiner—Tu T Nguyen
(74) Attorney, Agent, or Firm—Sughrue Mion, PLLC

(57) ABSTRACT

Analysis system including a central control section for generally controlling the analysis that sends a command to perform a pre-injection operation, to an automatic sampler together with information designating a sample to be selected, such as an identification number, and simultaneously sends a command to perform an operation of measuring a dark current in a photodiode array (PDA) detector, to a multi-channel spectrophotometer. Thus, the automatic sampler performs the pre-injection operation, such as an operation of moving a needle to a position of a designated vial container to suck a sample, and the spectrophotometer performs the dark-current measurement operation during a time period of the pre-injection operation. After the sample is actually introduced into the column, in response to a command to perform a normal measurement operation, an operation of acquiring absorption data of an eluate from the column is started without performing the dark-current measurement operation.

4 Claims, 3 Drawing Sheets

MC spectrophotometer in present invention

Conventional MC spectrophotometer

MC spectrophotometer in present invention

ANALYSIS SYSTEM

BACKGROUND OF THE INVENTION

1. Field of the Invention

The present invention relates to an analysis system which comprises an automatic sample feeding apparatus for selecting a sample to be analyzed (i.e., target sample) from a plurality of prepared samples, or changing a target sample, such as an automatic sampler or an automatic sample changer, and an optical measuring apparatus including a light detection device, such as a photodiode array detector. The analysis system of the present invention is suitable for a high performance liquid chromatograph or the like.

2. Description of the Related Art

A multi-channel spectrophotometer using a photodiode array detector as a light detection device is designed such that light having a given wavelength band is emitted to a sample, and wavelengths of transmitted light which has undergone absorption during passing of the emitted light through the sample are spectrally dispersed by a spectral dispersion device, such as a diffraction grating, whereafter an intensity of the light with the wide wavelength is concurrently detected by the photodiode array detector. This type of spectrophotometer is capable of measuring an absorption spectrum in a given wavelength band without mechanically rotating the diffraction grating. Therefore, it is commonly used as a light detection device of a high performance liquid chromatograph (HPLC), etc., as well as being used by itself.

In the above photodiode array (PDA) detector or a single-photodiode detector, a dark current flows even in a state when no light is entered into a light-receiving element (photodiode), to cause noise in measurement. As one countermeasure against this problem, before acquiring data reflecting light absorption of an intended sample, data about a dark current is acquired to perform a processing of correcting actual absorption data based on the acquired dark current data. As for an operation of measuring a dark current, there has been known a technique of arranging on a light path a shutter adapted to be selectively opened and closed in a mechanical manner, and measuring a dark current under a condition that the shutter is closed to block off light to be entered into the PDA detector, as disclosed, for example, the following Patent Document 1.

In a conventional HPLC equipped with the above multi-channel spectrophotometer using a photodiode array detector as a light detection device, the shutter is closed at the time of start of analysis, i.e., just after a sample is injected into a mobile phase to be fed to a column, so as to measure a dark current, and then opened after completion of the operation of measuring the dark current, so as to start acquiring absorption data of an eluate from the column, as disclosed in the following Patent Document 2. The shutter involves mechanical open and close movements, and it typically takes about 6 to 7 seconds as a dark-current measurement time required for completing the series of operations, i.e., closing the shutter→measuring the dark current→opening the shutter, after a command to measure a dark current is issued from a CPU. Generally, in the conventional HPLC, a time period from injection of a sample into the mobile phase through until a component of the sample is initially eluted from an outlet end of the column, is sufficiently greater than the dark-current measurement time.

Recent years, in connection with development of chromatography techniques primarily intended to provide enhanced throughput, a time period from injection of a sample into a mobile phase through until a component of the sample reaches a light detection device, has been drastically reduced. In some cases, it takes less than 10 seconds before a sample component is initially eluted off of a column. Thus, if the above conventional measurement technique is employed in such a multi-channel spectrophotometer, a part of sample components are likely to reach a light detection device before the operation of measuring a dark current is completed to establish a state capable of acquiring absorption data, which results in the preclusion of detection of the part of sample components.

[Patent Document 1] JP 08-122150A (paragraphs [0002] to [0005])

[Patent Document 2] JP 11-118781A (paragraph [0003])

SUMMARY OF THE INVENTION

In view of the above problem, it is an object of the present invention to provide an analysis system capable of reliably measuring a dark current in a PDA detector while avoiding occurrence of failing to measure a part of sample components due to the operation of measuring the dark current, for example, even if a time period required for component separation in a column is reduced, as mentioned above.

In order to achieve this object, the present invention provides an analysis system which comprises: an automatic sample feeding apparatus for selecting a designated sample from a plurality of prepared samples and reserving the selected sample as a target sample, or changing a target sample; an optical measuring apparatus including light source means for emitting light to a sample provided by the automatic sample feeding apparatus or a sample containing components of the provided sample, and light detection means for detecting light obtained through the sample in connection with the light emitted from the light source means; and a control apparatus for controlling the automatic sample feeding apparatus and the optical measuring apparatus. In the analysis system, the optical measuring apparatus includes light blocking means adapted to be selectively interposed in a light path between the light source means and the light detection means to block off the light emitted from the light source means, and dark-current measuring means operable to measure a dark current in the light detection means under a condition that the light emitted from the light source means is blocked off by the light blocking means, and the control apparatus is operable to control the automatic sample feeding apparatus and the optical measuring apparatus in such a manner that the optical measuring apparatus performs the operation of measuring the dark current, during a time period where the automatic sample feeding apparatus performs the operation of selecting/reserving or changing a target sample.

In the analysis system of the present invention, the automatic sample feeding apparatus may be an automatic sampler or an automatic sample changer. The optical measuring apparatus may be an ultraviolet-visible spectrophotometer or an infrared spectrophotometer. Further, the optical measuring apparatus may be any other type using a light detection device which involves a problem about a dark current.

In the operation of measuring a dark current, the light blocking means in the optical measuring apparatus is required to block off light emitted from the light source means so as to allow the dark-current measuring means to acquire a signal corresponding to a dark current, and then release the light blocking. If the light blocking means is composed of a mechanical shutter, it takes a certain time, e.g., about several seconds, to open and close the shutter. In the automatic sample feeding apparatus, the operation of selecting/reserving or changing a sample also involves a mechanical movement, and a time period required for this movement is greater than the time period required for the operation of measuring a dark current. That is, before the automatic sample feeding apparatus completes the operation of selecting/reserving or changing a target sample, the optical measuring apparatus completes the operation of measuring the dark current. Thus, immediately after completion of the operation of selecting/reserving or changing a target sample (or an operation of providing or feeding a target sample), an operation of acquiring data reflecting optical characteristics of the sample, such as light absorption, can be started.

In one specific embodiment of the present invention, the analysis system is a liquid chromatography system comprising a column for separating components of a sample provided by the automatic sample feeding apparatus. In this case, the light source means may be operable to emit light to an eluate eluted from an outlet end of the column, and the light detection means may be operable to detect transmitted light which has undergone absorption during passing of the emitted light through the eluate.

In this analysis system, the optical measuring apparatus may further include spectral dispersion means for spectrally dispersing wavelengths of the transmitted light which has undergone absorption during passing of the emitted light through the eluate, wherein the light detection means is a photodiode array detector operable to detect light wavelength-dispersed by the spectral dispersion means.

In the analysis system according to the above specific embodiment, the automatic sample feeding apparatus may be an automatic sampler which comprises a holding section for holding a plurality of vial containers each containing a different sample solution, a driving mechanism for selecting one of the vial containers held by the holding section and moving a sample-sucking needle to a position of the selected vial container, a sample-reserving section for temporarily reserving the sample sucked by the needle, and an injection section for injecting the sample reserved in the sample-reserving section into a mobile phase, to allow the sample to be fed to a column. This automatic sampler is operable, in response to receiving an instruction for selecting and reserving a target sample, from the control apparatus, to move the needle by the driving mechanism to suck the sample, and reserve the sucked sample in the sample-reserving section.

In conjunction with the above instruction to the automatic sample feeding apparatus, the control apparatus is operable to instruct the optical measuring apparatus to measure a dark current. In response to this instruction, the light blocking means is operable to block off light to be entered into the light detection means, and the dark-current measuring means is operable to acquire a detection signal corresponding to a dark current at the time. In this manner, the instruction for selecting and reserving a target sample and the instruction for measuring a dark current are approximately simultaneously issued. This makes it possible to reliably complete the operation of measuring a dark current before completion of the operation of selecting and reserving a target sample.

In the analysis system according to the above embodiment, the optical measuring apparatus may further include measurement execution means for performing an operation of normally measuring the transmitted light without performing the operation of measuring the dark current, wherein the control apparatus is operable to instruct the automatic sample feeding apparatus to select/reserve or change a target sample, and instruct the optical measuring apparatus to measure the dark current, and, after the automatic sample feeding apparatus completes selecting/reserve or changing the target sample, to instruct the automatic sample feeding apparatus to feed the sample to the column, and instruct the optical measuring apparatus to start the operation of normally measuring the transmitted light.

According this feature, at approximately the same time as, i.e., almost without a temporal delay relative to, introducing a sample from the automatic sample feeding apparatus into a column, the light detection means can obtain a signal reflecting a light absorption of an eluate eluted from the outlet end of the column. Thus, even if a part of components of the sample are eluted through the column within a short time, the components of the sample can be reliably detected without failing to detect such components, to obtain an absorption spectrum.

As above, in the analysis system of the present invention, for example in a liquid chromatography system, the operation of measuring a dark current can be completed before introducing a sample into a column, so that the need for measuring a dark current after injection of a sample as in the conventional technique is eliminated. Thus, even if a part of components of a sample injected into a mobile phase are rapidly eluted through the column, the sample components can be reliably detected. In addition, an accurate dark current has already been obtained through the operation of measuring a dark current. Thus, based on this measurement result, an absorption spectrum free of an influence of the dark current can be calculated.

DESCRIPTION OF THE EXEMPLARY EMBODIMENTS

Figure 1:
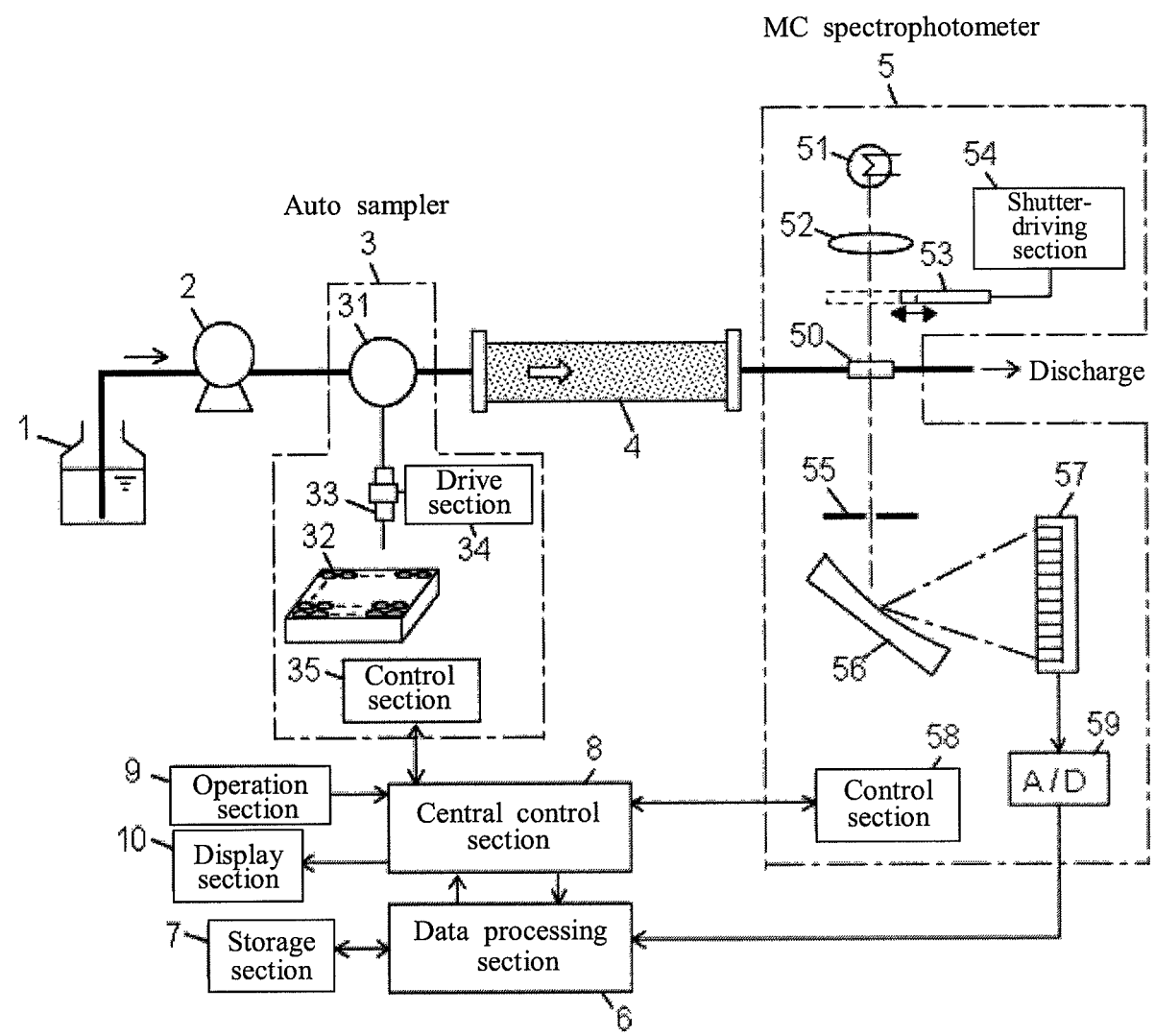
FIG. 1 is a fragmentary block diagram schematically showing a high performance liquid chromatography (HPLC) system according one embodiment of the present invention.
Figure 2A:
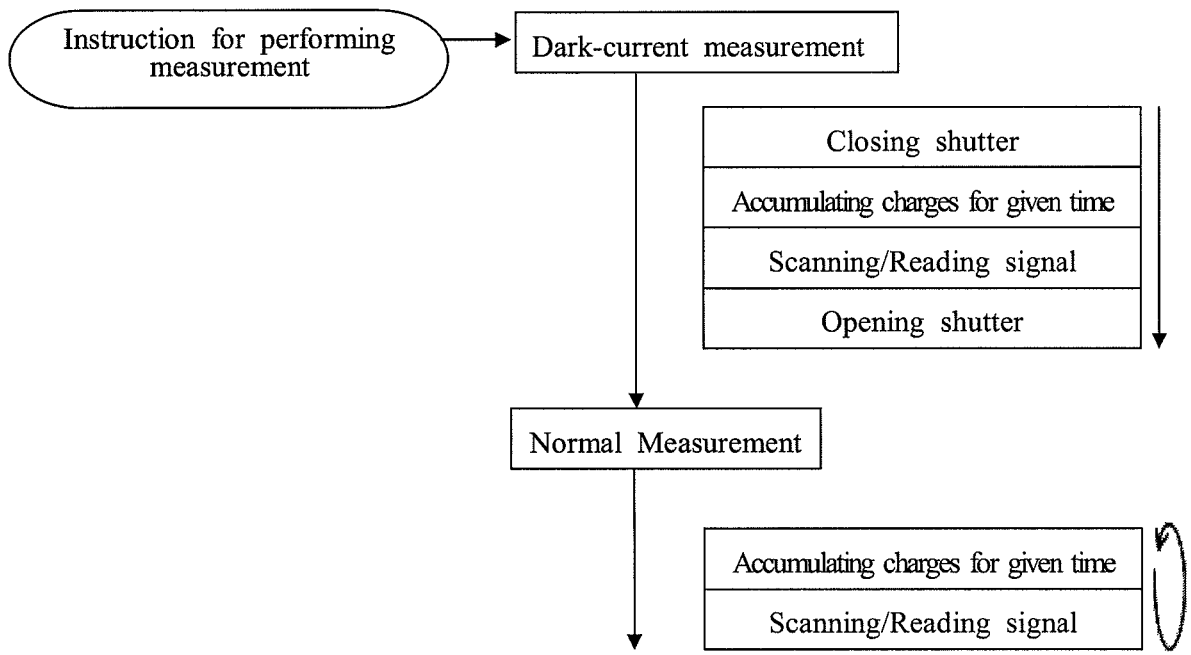
FIGS. 2A and 2B are explanatory diagrams showing a difference in control of measurement operations between a multi-channel spectrophotometer in the HPLC system according the embodiment and a conventional multi-channel spectrophotometer.
Figure 2B:
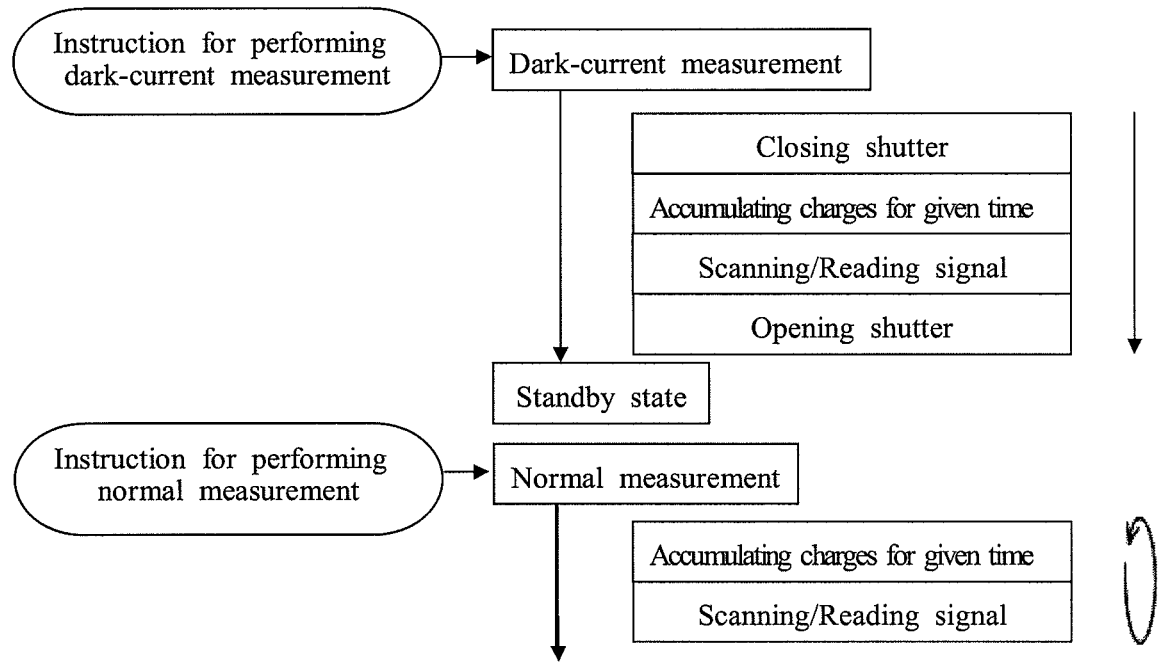
Figure 3:
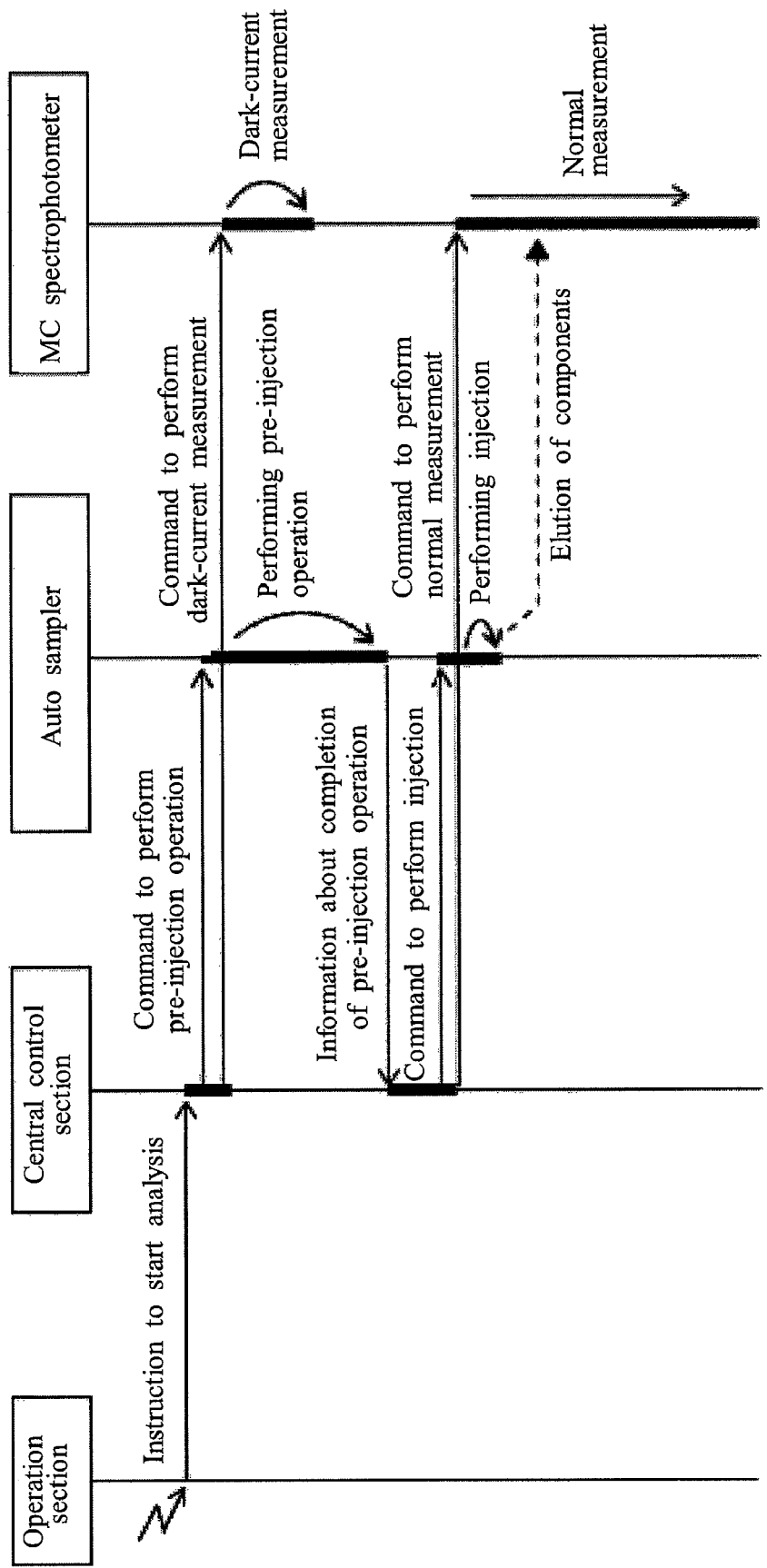
FIG. 3 is an explanatory control sequence diagram showing a distinctive operation in the HPLC system according the embodiment.

With reference to the drawings, the present invention will now be described based on a high performance liquid chromatography (HPLC) system according one embodiment thereof. FIG. 1 is a fragmentary block diagram schematically showing the HPLC system according the embodiment. FIGS. 2A and 2B are explanatory diagrams showing a difference in control of measurement operations between a multi-channel spectrophotometer in the HPLC system according the embodiment and a conventional multi-channel spectrophotometer, and FIG. 3 is an explanatory control sequence diagram showing a distinctive operation in the HPLC system according the embodiment.

The HPLC according to this embodiment comprises a mobile phase container 1 containing a mobile phase, a liquid feed pump 2, an automatic sampler 3, and a column 4. The liquid feed pump 2 is operable to suck the mobile phase contained in the mobile phase container 1 and feed the sucked mobile phase to a column 4 via an injector 31 of the automatic sampler 3 at an approximately constant flow rate. In addition to the injector 31, the automatic sampler 3 includes, a sample rack 32 storing a large number of vial containers, a needle 33 for sucking a sample solution from a selected one of the vial containers, a drive section 34 for moving the needle 33 to a position above any one of the vial containers and then vertically moving the needle 33, and a control section 35 having a CPU and for controlling respective operations of valves or driving sources for driving the drive section 34 and a measuring syringe (not shown) incorporated in the injector 31.

The HPLC also comprises a multi-channel spectrophotometer 5 provided at an outlet end of the column 4 to detect sample components in an eluate from the column 4. The multi-channel spectrophotometer 5 includes a transparent flow cell 50 for allowing an eluate to pass therethrough, a light source 51, a condenser lens 52 for condensing light emitted from the light source 51 in such a manner as to be led to the flow cell 50, a shutter 53 adapted to be selectively interposed in a light path between the condenser lens 52 and the flow cell 50 according to driving of a shutter-driving section 54 having a driving motor, an inlet slit 55 for allowing light transmitted through the flow cell 50 to pass therethrough, a concave diffraction grating 56 for spectrally dispersing wavelengths of light, a photodiode array (PDA) detector 57 for approximately concurrently detecting wavelength-dispersed light, a control section 58 having a CPU and for controlling an operation of turn on/off the light source 51, an operation of driving the shutter-driving section 54, and an operation of reading a signal from the PDA detector 57, and an A/D convertor 59 for converting a detection signal of the PDA detector 57 into a digital value.

The HPLC also comprises a data processing section 6, a storage section 7 and a central control section 8. The detection signal converted into a digital value through the A/D convertor 59 is input into the data processing section 6, and temporarily stored in the storage section 7. Then, a data processing is executed according to a given algorithm to create an absorption spectrum or the like, based on the detection signal. The central control section 8 is internally provided with a CPU, a ROM and a RAM, and connected to an operation section 9, such as a keyboard adapted to be operated by an analysis operator, i.e., a person assigned to carry out an analysis, and a display section 10 for displaying a measurement result and others. The central control section 8 is operable to control the control sections 35, 58, the liquid fed pump 2, and a column oven (not shown) housing the column 4. A general-purpose personal computer may be used as hardware of each of the central control section 8 and the data processing section 6, and a part or most of the functions of the central control section 8 and the data processing section 6 may be achieved by executing control/processing software pre-installed in the personal computer.

With reference to FIGS. 2A and 2B, a difference between respective control sequences of the multi-channel spectrophotometer 5 in this embodiment and a conventional multi-channel spectrophotometer will be described below.

As shown in FIG. 2A, a control sequence for the conventional multi-channel spectrophotometer is configured such that an operation of measuring a dark current is performed in response to a measurement execution command (instruction) externally given thereto, and a normal measurement operation is performed subsequently to completion of the dark-current measurement operation. More specifically, in the dark-current measurement operation, the shutter is closed to block off light to be entered into the PDA detector, and electric charges will be accumulated in each of the photodiodes of the PDA detector for a given time period under a condition that the shutter is closed. The electric charges to be accumulated under this condition are caused by a dark current. After elapse of the electric charge accumulation period, a detection signal based on the accumulated signal charge is read from each of the photodiodes while sequentially scanning the photodiodes. After completion of the operation of reading the detection signals, the shutter is opened to allow light to be entered into the PDA detector. In the subsequent normal measurement operation, the steps of allowing electric charges to be accumulated in each of the photodiodes of the PDA detector for a given time period under a condition that light is entered into the PDA detector, and, after elapse of the electric charge accumulation period, reading a detection signal based on the accumulated signal charge, from each of the photodiodes while sequentially scanning the photodiodes are repeated.

In contrast, as shown in FIG. 2B, in the multi-channel spectrophotometer 5 in this embodiment, two commands consisting of a dark-current measurement command, i.e., instruction for performing only the dark-current measurement operation, and a normal measurement command, i.e., instruction for performing only the normal measurement operation. More specifically, when the dark-current measurement command is given to the multi-channel spectrophotometer 5, the shutter 53 is closed according to driving of the shutter-driving section 54 to close to block off light to be entered into the PDA detector 57, and electric charges will be accumulated in each of the photodiodes of the PDA detector 57 for a given time period under a condition that the shutter 53 is closed. After elapse of the electric charge accumulation period, a detection signal based on the accumulated signal charge is read from each of the photodiodes while sequentially scanning the photodiodes. After completion of the operation of reading the detection signals, the shutter 53 is opened to allow light to be entered into the PDA detector 57, and the shutter-driving section 54 is placed in a standby state.

When the normal measurement command is given to the multi-channel spectrophotometer 5, the steps of allowing electric charges based on light entered into the PDA detector 57 to be accumulated in each of the photodiodes of the PDA detector 57 for a given time period, without performing the dark-current measurement operation, and, after elapse of the electric charge accumulation period, reading a detection signal based on the accumulated signal charge, from each of the photodiodes while sequentially scanning the photodiodes are repeated.

As above, in the multi-channel spectrophotometer 5 of the HPLC system according to this embodiment, the dark-current measurement command and the normal measurement command are provided independently. That is, each of the dark-current measurement operation and the normal measurement operation can be performed in an independent manner and at any timing.

With reference to FIG. 3, a distinctive operation in the HPLC system according the embodiment will be described below. The following description will be made on an assumption that a large number of vial containers each continuing a sample solution in advance are stored in the sample rack 32 of the automatic sampler 3, and identification information, such as serial numbers, are given to the respective vial containers.

An analysis operator manually operates the operation section 9 to designate the identification information of a target sample solution, and instruct to start an analysis. In response to receiving this instruction, the central control section 8 sends a command to perform a pre-injection operation, to the automatic sampler 3, and simultaneously sends the dark-current measurement command to the multi-channel spectrophotometer 5. In response to receiving the command to perform the pre-injection operation, the control section 35 operates to perform a preparatory operation of sucking the sample solution from the designated vial container in order to inject the sucked sample solution from the injector 31 into the mobile phase. Specifically, the drive section 34 moves the needle 33 to a position above the designated vial container and then moves the needle 33 downwardly in such a manner as to allow the needle 33 to be immersed into the sample solution of the vial container. Then, the measuring syringe is operated to suck the sample solution into a sample loop within the injector 31 through the needle 33, and hold the sample solution in the sample loop. Although a time period required for reserving the sample solution in the sample loop slightly varies depending on a position of a designated vial container, it typically takes about several ten seconds, more specifically 10 seconds or more at the minimum.

In response to receiving the dark-current measurement command, the control section 58 in the multi-channel spectrophotometer 5 instructs the shutter-driving section 54 to close the shutter 53 to block off light to be entered into the flow cell 50, which is also shown in FIG. 2B. Thus, no light is entered into the PDA detector 57. Under this condition, each of the photodiodes of the PDA detector 57 is scanned to acquire a detection signal arising from a dark current in each of the photodiodes, and the acquired detection signals are sent to the data processing section 6 via the A/D converter 59. After completion of the operation of acquiring the dark current signals, the control section 58 instructs the shutter-driving section 54 to open the shutter 53. A time period required for the dark-current measurement operation is dominated largely by a time period required for closing and opening the shutter 53, and typically about several seconds, more specifically 10 seconds or less at the maximum. Thus, it is guaranteed that the dark-current measurement operation is surely completed before completion of the pre-injection operation in the automatic sampler 3. In the data processing section 6, background spectra data corresponding to the dark current is stored in the storage section 7 to complete the dark-current measurement operation, and then the multi-channel spectrophotometer 5 is placed in a standby state.

When the sample solution is reserved in the sample loop of the injector 31, the control section 35 of the automatic sampler 3 sends information about completion of the pre-injection operation, to the central control section 8. In response to receiving this information, the central control section 8 sends a command to perform an operation of injecting a sample solution, to the automatic sampler 3, and simultaneously sends the normal measurement command to the multi-channel spectrophotometer 5. In response to receiving the command to perform the sample-solution injection operation, the control section 35 of the automatic sampler 3 operates to switch a valve of the injector 31 to allow the mobile phase to pass through the sample loop holding the sample solution so as to push out the sample solution from the sample loop and introduce the sample solution into the column 4.

Concurrently, the control section 58 of the multi-channel spectrophotometer 5 operates to start the normal measurement operation, which is also shown in FIG. 2B. Specifically, a detection signal corresponding to light which has undergone absorption during passing through the flow cell 50 is read from each of the photodiodes (light-receiving elements) of the PDA detector 57 while scanning the respective photodiodes, and the read detection signals are sent to the data processing section 6 via the A/D converter 59. Components of the sample solution introduced into the column 4 are temporally separated, and sequentially eluted from the outlet end of the column 4. This eluate passes through the flow cell 50, and therefore spectra data to be repeatedly sent from the multi-channel spectrophotometer 5 to the data processing section 6 reflects a type and concentration of each of the sample components contained in the eluate.

In the data processing section 6, the above spectra data are temporarily stored in the storage section 7. Then, the previously-stored background spectra data corresponding to the dark current is subtracted from the spectra data to derive data free of an influence of the dark current, so as to create a final absorption spectrum, and the absorption spectrum is displayed on the display section 10.

As above, in the HPLC system according to this embodiment, the dark-current measurement operation has already been completed before a sample is introduced into the column 4, so that the operation of acquiring data reflecting a light absorption characteristic of an eluate from the column 4 can be started at approximately the same timing of sample injection, without performing the dark-current measurement operation after the sample injection. Thus, even if a part of components of the sample introduced into the column 4 are eluted through the column 4, for example, within about several seconds, data about the part of components can also be reliably acquired without occurrence of failure in data acquisition.

In cases where subsequently to completion of a liquid chromatography (LC) analysis for one sample, an LC analysis for another sample stored in another vial container is performed, it is necessary to take a certain time for the pre-injection operation. Thus, the dark-current measurement operation can be performed within the time period of the pre-injection operation. This makes it possible to calculate a highly accurate absorption spectrum by constantly using spectra data about a latest dark current.

By way of exception, in an analysis system employing an overlap injection operation as disclosed, for example, in JP 2005-257575A, before a previous sample is fully eluted off of a column, a next sample is introduced into the column. Thus, it is necessary to acquire measurement data of an eluate from the column even during the time period of the pre-injection operation. Therefore, there is not an enough time to perform the dark-current measurement operation between two LC analyses. In this case, a result of the dark-current measurement operation performed during the time period of the pre-injection operation for the first sample will be used for calculating an absorption spectrum in each of a series of subsequent measurements.

Although the above embodiment has been described based on one example where the present invention is applied to the HPLC system, it is not essential for the present invention to separate sample components using a column. For example, the present invention can be generally applied to an analysis system using any other type of optical measuring apparatus comprising an automatic sampler (or automatic sample changer) for appropriately changing a target sample, wherein it is necessary for the operation of changing a target sample to take a certain time equal to or greater than at least a time required for the dark-current measurement operation. Thus, the light detection means is not limited to the PDA detector, but may be any other type of detector using a photoelectric conversion element involving a problem about a dark current, such as a single-photodiode detector.

What is claimed is:

1. An analysis system comprising:
    an automatic sample feeding apparatus for selecting a designated sample from a plurality of prepared samples and reserving said selected sample as a target sample, or changing a target sample;
    an optical measuring apparatus including light source means for emitting light to a sample provided by said automatic sample feeding apparatus or a sample containing components of said provided sample, and light detection means for detecting light obtained through said sample in connection with said light emitted from said light source means; and a control apparatus for controlling said automatic sample feeding apparatus and said optical measuring apparatus, wherein:

said optical measuring apparatus includes light blocking means adapted to be selectively interposed in a light path between said light source means and said light detection means to block off said light emitted from said light source means, and dark-current measuring means operable to measure a dark current in said light detection means under a condition that said light emitted from said light source means is blocked off by said light blocking means; and said control apparatus is operable to control said automatic sample feeding apparatus and said optical measuring apparatus in such a manner that said optical measuring apparatus performs said operation of measuring said dark current, during a time period where said automatic sample feeding apparatus performs said operation of selecting, reserving or changing a target sample.

2. The analysis system as defined in claim 1, which is a liquid chromatography system comprising a column for separating components of a sample provided by said automatic sample feeding apparatus, wherein:

said light source means is operable to emit light to an eluate eluted from an outlet end of said column; and said light detection means is operable to detect transmitted light which has undergone absorption during passing of said emitted light through said eluate.

3. The analysis system as defined in claim 2, wherein said optical measuring apparatus further includes spectral dispersion means for spectrally dispersing wavelengths of said transmitted light which has undergone absorption during passing of said emitted light through said eluate, wherein said light detection means is a photodiode array detector operable to detect light wavelength-dispersed by said spectral dispersion means.

4. The analysis system as defined in claim 2, wherein said optical measuring apparatus further includes measurement execution means for performing an operation of normally measuring said transmitted light without performing said operation of measuring said dark current, wherein said control apparatus is operable to instruct said automatic sample feeding apparatus to selecting, reserving or change a target sample, and instruct said optical measuring apparatus to measure said dark current, and, after said automatic sample feeding apparatus completes selecting, reserving or changing said target sample, to instruct said automatic sample feeding apparatus to feed said sample to said column, and instruct said optical measuring apparatus to start said operation of normally measuring said transmitted light.

* * * * *